United States Patent
Hirose et al.

(10) Patent No.: US 7,020,306 B2
(45) Date of Patent: Mar. 28, 2006

(54) POLISHING PAD SURFACE CONDITION EVALUATION METHOD AND AN APPARATUS THEREOF AND A METHOD OF PRODUCING A SEMICONDUCTOR DEVICE

(75) Inventors: Takenori Hirose, Machida (JP);
Hiroyuki Kojima, Kawasaki (JP);
Mineo Nomoto, Yokohama (JP);
Susumu Aiuchi, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 769 days.

(21) Appl. No.: 09/774,723

(22) Filed: Feb. 1, 2001

(65) Prior Publication Data
US 2001/0015801 A1    Aug. 23, 2001

(30) Foreign Application Priority Data
Feb. 8, 2000    (JP) .......................... 2000-035616

(51) Int. Cl.
*G06K 9/00*    (2006.01)
(52) U.S. Cl. ..................... 382/108; 382/143; 382/145
(58) Field of Classification Search ............... 382/108, 382/141, 143–151; 451/8, 10, 443, 444, 451/285, 287, 288; 356/237.1, 237.2, 600; 348/86, 87, 125, 128
See application file for complete search history.

(56) References Cited

U.S. PATENT DOCUMENTS

| | | | | |
|---|---|---|---|---|
| 5,643,050 A | * | 7/1997 | Chen ........................... | 451/10 |
| 5,708,506 A | * | 1/1998 | Birang ........................ | 356/600 |
| 6,004,196 A | * | 12/1999 | Doan et al. ................. | 451/443 |
| 6,102,776 A | * | 8/2000 | Boggs et al. ................. | 451/8 |
| 2002/0063860 A1 | * | 5/2002 | Jun et al. ................. | 356/237.2 |

OTHER PUBLICATIONS

Doi et al, "Semiconductor Planarizing CMP Technology" (6 pages: translation of portion believed to be relevant).

* cited by examiner

*Primary Examiner*—Vikkram Bali
(74) *Attorney, Agent, or Firm*—Mattingly, Stanger, Malur & Brundidge, P.C.

(57) ABSTRACT

The object of the present invention is to establish a technology for directly evaluating polishing pad surface conditions, to allow high-precision CMP process management, and to improve process throughput. The pad surface is illuminated with light. The intensity of reflected light or fluorescence from the illuminated area or an intensity distribution image is used directly evaluate the pad surface condition. Based on the results of this evaluation, conditioning conditions for a conditioner are optimized, thus allowing high-precision CMP processing while maintaining good pad surface conditions.

11 Claims, 12 Drawing Sheets

POLISHING PAD SURFACE CONDITION EVALUATION METHOD AND AN APPARATUS THEREOF AND A METHOD OF PRODUCING A SEMICONDUCTOR DEVICE

BACKGROUND OF THE INVENTION

The present invention relates to a method for evaluating polishing pad surface conditions, a device for the same, and a method for producing thin film devices using the same.

Polishing pads are commonly used in the polishing process of production lines for various electronic parts. A method used in semiconductor device production lines, in which a surface is polished to be plane through chemical and mechanical operations (CMP: Chemical Mechanical Polishing), will be described below as a representative example of a polishing process.

Semiconductor devices are produced by forming devices and wiring patterns on a silicon wafer through deposition, lithography, etching, and the like. In recent years, there has been a growing trend toward miniaturization and multi-layering to provide higher precision and higher densities in devices.

As a result, unevenness of a wafer surface has increased. Such unevenness of a wafer surface makes lithography, which is indispensable for forming wiring patterns and the like, difficult. Thus, planerizing the wafer surface is need. A polishing process method involving CMP is used for this.

An important issue in CMP processing is the management of pad surface conditions used in the polishing process. However, no effective method for performing direct evaluation has been established. Conventionally, pad surface conditions are evaluated indirectly based on changes in polishing rates. The polishing rate is calculated from the polishing amount, generally determined by measuring the film thickness of the item being polished before and after CMP processing, and the processing time in which the actual processing was performed.

An example of this type of conventional technology relating to CMP processing is presented in "Semiconductor planarizing CMP technology" (Doi, Kawanishi, Nakagawa, Kougyouchousakai Ltd.).

Figure 1:
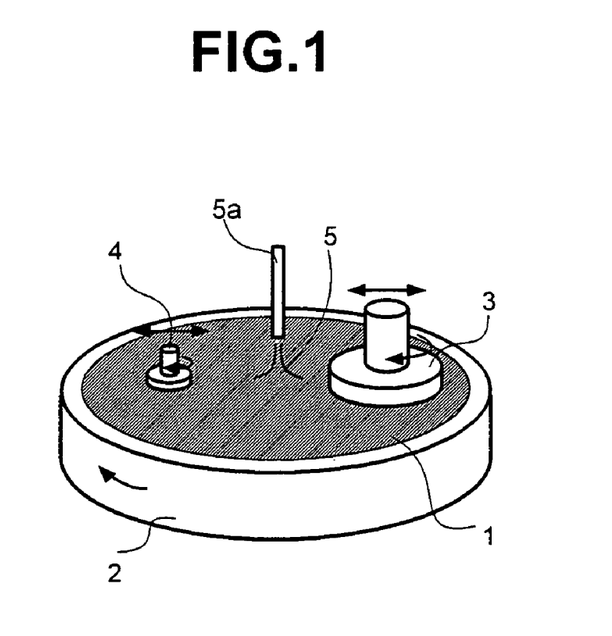
FIG. 1 is a schematic drawing showing an example of a CMP process.

CMP processing is generally performed using a processing device shown schematically in FIG. 1. The device includes a polishing pad 1 (hereinafter referred to as pad) and a rotating polishing turntable 2 on which the pad 1 is mounted. A wafer chuck 3 supports the wafer and can move radially over the pad 1 while turning. A conditioner 4 corrects pad deterioration and, like the wafer chuck, moves radially over the pad while spinning. A slurry 5 is used for polishing and is supplied to the pad from a supply nozzle 5a.

In CMP processing, if a single pad is used to polish a large number of wafers, the pad will deteriorate and the polishing rate will decrease. This reduction of polishing rate results from the fact that the planarity of the pad surface increases as wafers are polished.

This deterioration does not occur uniformly on the pad surface. The deterioration on the pad 1 can form a concentric area 6 as shown in the plan drawing in FIG. 2, spotting 6a as shown in the plan drawing in FIG. 17, or the like. In these figures, areas 7 indicate good areas where there is little deterioration.

Figure 2:
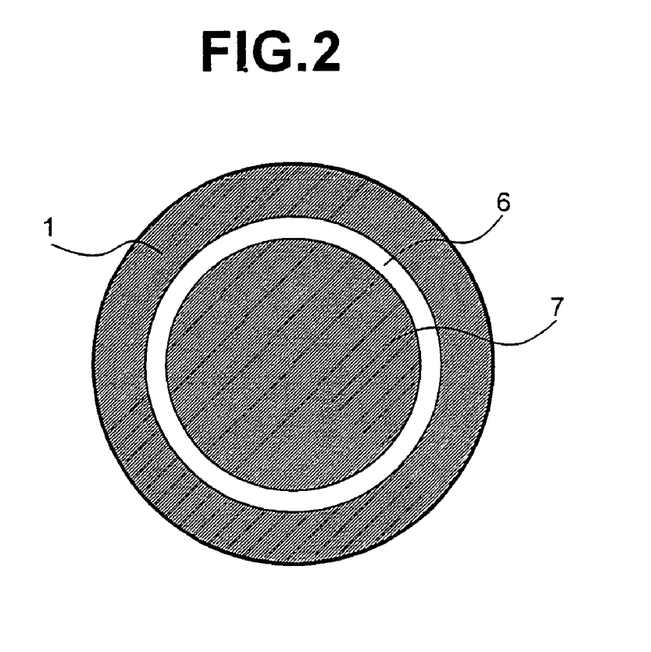
FIG. 2 is a schematic drawing showing an example of distribution of pad deterioration.

In the former case, the concentric area 6 is believed to occur because the pad 1 and the wafer (supported by the wafer chuck 3 but not shown in the figure) in FIG. 1 are both circular. Thus, different degrees of wafer processing take place depending on the radial position on the pad.

Figure 17:
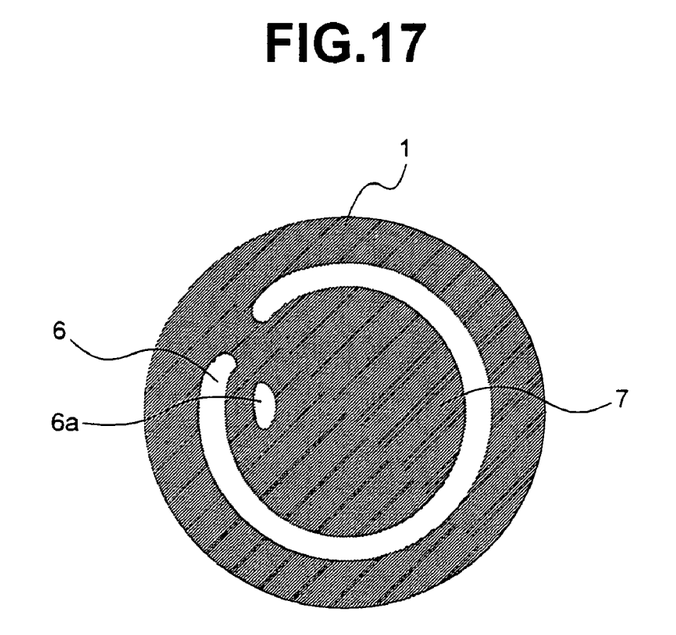
FIG. 17 is a schematic drawing showing an example of pad deterioration distribution.

In the latter case, the spotting 6a is believed to occur because of bad attachment of the pad 1 to the polishing turntable 2, e.g., air entering during attachment, or localized defects in the pad itself.

In CMP processing, conditioning is performed between processes or during a process in response to pad deterioration. Conditioning refers to cutting the planarized pad surface to increase surface roughness and restore the polishing rate.

One method involves cutting the surface of the pad 1 with a conditioner 4 having a surface on which particles such as diamonds are adhered, thus increasing pad surface roughness.

As the pad surface deteriorates, the uniformity of the wafer surface and processing variations between wafers will be affected. For example, if the concentric area 6 deteriorates as shown in FIG. 2, the wafer center, which is always in contact with the deteriorated area, will have a different polishing rate from the outer area. As a result, the wafer center and the outer perimeter will be processed to different degrees.

In response to problems such as these, there is a need to optimize conditioning conditions by evaluating pad surface conditions. However, the conventional evaluation method is an indirect method that evaluates pad surface conditions from changes in polishing rates calculated from a processing amount calculated from the film thickness before and after polishing and the processing time.

With this type of indirect method, the pad surface conditions cannot be accurately evaluated. Also, evaluation requires time and cannot be performed in response to sudden problems, thus resulting in many defects.

Also, when a single pad has been used for a certain amount of processing, the polishing rate of the pad will not be restored even when conditioning is performed. This condition indicates that the pad has reached its life span and that the pad needs to be replaced. In terms of reducing costs in CMP processing, it would be desirable to maximize the number of wafers processed by a single polishing pad. However, indirect evaluation based on polishing rates will not provide an accurate evaluation of pad surface conditions and there are variations in the polishing rates themselves. Thus, the pad life span cannot be accurately evaluated, resulting in pads being replaced before their life span is reached.

SUMMARY OF THE INVENTION

The embodiments of the present invention eliminate the problems of the conventional technology described above and provide a method for evaluating polishing pad surface conditions that directly evaluates the polishing pad surface conditions, a device for the same, and a method for producing thin-film devices using the same.

Semiconductor devices are representative examples of thin-film devices. In addition, thin-film devices can be various other electronic parts, e.g., liquid crystal devices, that require planarizing through high degrees of polishing.

In order to achieve the objects described above, the present invention directly evaluates deterioration of the pad surface due to polishing. Light is used to illuminate the polishing pad surface, and the optical information signal detected from this illuminated region is used to evaluate the surface condition of the polishing pad.

In other words, in this method for evaluating polishing pad surface conditions, light is used to illuminate the pad surface, and the deterioration of the pad surface is evaluated using the pad surface image or the intensity of the reflected light or the like from the illuminated area of the pad. The evaluation technology described above is used to optimize the conditioning conditions with which the conditioner is used to restore the pad surface condition.

Also, the polishing pad surface condition evaluation technology is used to implement accurate evaluation of pad life span. Also, by equipping a polishing device with this evaluation device, the planarity of the processed object, e.g., wafers in semiconductor production, can be improved and throughput can be increased.

The following is a description of a representative example of how the present invention can be implemented in a semiconductor device production process.

In a process for polishing a film formed on the surface of a semiconductor device, light is used to illuminate the pad surface. The light reflected from the illuminated area is detected, and the detected pad surface image or the intensity of the reflected light is used to accurately evaluate the polishing pad surface condition. Alternatively, excitation light is used to illuminate the polishing pad, the fluorescence generated by the polishing pad is detected, and the detected pad surface image or the intensity of the fluorescence is used to accurately evaluate the polishing pad surface condition.

Also, with the method for evaluating the pad surface condition, positions on the pad surface can be evaluated so that the distribution of deterioration on the pad surface can be accurately evaluated.

Also, the CMP process can be made stable and optimized using the pad surface evaluation results.

Furthermore, in a method for producing thin-film devices wherein a thin film is formed on a substrate, the surface of the substrate is planarized by using a polishing pad to polish the surface of the substrate on which the thin film is formed, the planarized substrate is cleaned, resist is applied to the cleaned substrate, and a pattern is exposed, the present invention restores the surface condition of the polishing pad during the planarizing step. The surface of the polishing pad used to polish the surface of the substrate is illuminated with light. The light reflected from the polishing pad due to this illumination is detected. A detection signal from this reflected light is used to evaluate the deterioration of the surface of the polishing pad. The evaluation results are used to restore the surface conditions of the polishing pad.

These and other objects, features and advantages of the invention will be apparent from the following more particular description of preferred embodiments of the invention, as illustrated in the accompanying drawings.

DESCRIPTION OF THE PREFERRED EMBODIMENTS

The following is a description of specific embodiments of the present invention.

This description will use as an example a polishing process in which the item to be polished is a thin film with an uneven surface is formed on a substrate, and a polishing pad is used to polish the surface and make it planarized. An illumination light source is selected according to the structure of a detection optical surface, e.g., a monochromatic light such as a laser light source or a white light such as a halogen lamp.

First, six representative examples of how the surface condition of the polishing pad is evaluated will be described.

(1) During the polishing process, a light such as a monochromatic laser light is used to illuminate the surface of the polishing pad. The light reflected from the illuminated region of the polishing pad is detected using an optical system. The surface condition of the polishing pad is evaluated based on the detected intensity of the reflected light.

(2) The polishing pad surface is illuminated with a light, and the surface image of the illuminated region is detected by an optical system. The surface condition of the polishing pad is evaluated based on the detected image signal.

(3) The polishing pad surface is illuminated with a light, and the surface image of the illuminated region is detected by an optical system. Bi-level conversion is performed on the detected image signal. The surface condition of the polishing pad is evaluated based on the area ratio of the resulting bi-level image.

(4) The polishing pad surface is illuminated with an excitation light. The fluorescence generated from the region illuminated by the excitation light is detected. The surface condition of the polishing pad is evaluated based on the intensity of the detected fluorescence.

(5) The polishing pad surface is illuminated with an excitation light. The pad surface image formed by the fluorescence generated from the region illuminated by the excitation light is detected. The surface condition of the polishing pad is evaluated based on the detected image signal.

(6) The polishing pad surface is illuminated with an excitation light. The pad surface image formed by the fluorescence generated from the region illuminated by the excitation light is detected. Bi-level conversion is performed on the detected image signal. The surface condition of the polishing pad is evaluated based on the area ratio of the resulting bi-level image.

A device for evaluating the surface condition of a polishing pad according to the present invention includes: means for illuminating illuminating a polishing pad surface with a light; means for detecting detecting optical information from an illuminated region of the polishing pad; and means for processing evaluating the surface condition of the polishing pad based on a detected optical information signal.

Figure 18:
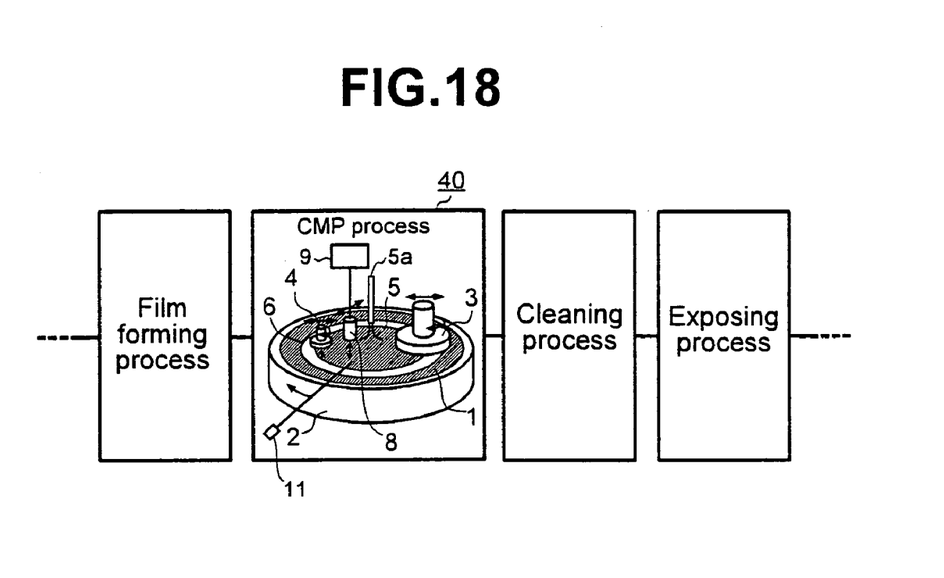
FIG. 18 is a schematic drawing showing a section of a semiconductor production process.

Referring to FIG. 18, the device for evaluating the surface condition of a polishing pad will be described in detail. This figure is a schematic diagram of a polishing pad surface condition evaluating device 40 according to the present invention used in a CMP process in the production process for semiconductor devices.

A CMP polishing device is formed with a structure that is widely known in the art. A polishing pad 1 is mounted on a rotating polishing turntable 2. On the polishing pad 1, a wafer chuck 3 and a conditioner 4 for correcting pad deterioration are rotated independently and placed in contact with the pad 1 with a predetermined pressure. The wafer chuck 3 and the conditioner 4 move in a reciprocating manner along the radius of the pad 1.

In the polishing process, a wafer (not shown in the figure) is the object to be polished and is supported by the wafer chuck 3. A polishing fluid (slurry) 5 is supplied to the pad 1 through a supply nozzle 5a to perform polishing. The polishing pad surface condition evaluation device 40 according to the present invention, described below, detects the surface condition of the pad 1 during polishing or while the polishing is temporarily interrupted. The detection output is sent directly to the conditioner 4 as feedback to optimize conditioning conditions.

More specifically, the detection output is used to select operations performed by the conditioner 4 such as conditioning pressure, rotation speed, and the period of the reciprocating motion, as well as the tool (conditioner) used in conditioning, and the like.

The polishing pad surface condition evaluation device 40 according to the present invention includes: means for illuminating, indicated by a light source 11; means for detecting optical information from an illuminated region of the polishing pad, indicated by a detector 8; and means for processing evaluating the surface condition of the polishing pad based on an optical information signal detected by the detector 8, indicated by a signal processor 9.

Detecting means detecting optical information is formed from detecting means detecting not only light reflected from an illuminated region but also fluorescence and/or surface images.

Detecting means detecting optical information, indicated by the detector 8, includes an optical system collecting optical information and a detector detecting the optical information, e.g., a CCD camera. These structures will be described more specifically in the embodiments below.

If detecting means detecting optical information is detecting means detecting surface image information from the illuminated region as described above, then processing means indicated by the signal processor 9 is formed as processing means that performs bi-level conversion on an image signal detected by detecting means and evaluates the surface condition of the polishing pad based on the area ratio of the resulting bi-level image.

In the CMP polishing device, the output signal from the polishing pad surface condition evaluation device 40 is used as feedback as described above to at least the conditioner 4 so that conditioning conditions (the contact pressure of the conditioner 4 on the pad, the rotation speed of the conditioner 4 and the polishing turntable 2, the period of the reciprocating motion, and the conditioner material used for conditioning) and the like are selected appropriately based on the detection output.

The method for producing thin-film devices according to the present invention includes: a process for using a polishing pad to polish and form a planarized surface on an item to be polished, in the form of a thin film having a rough surface and formed on a wafer substrate; and a process for evaluating the surface condition of the polishing pad and optimizing conditioning conditions performed on the polishing pad using a conditioner based on the evaluation results. The evaluation of the surface condition of the polishing pad is performed using the polishing pad surface condition evaluation methods described above.

Out of the semiconductor device production processes, the processes before and after this planarizing process is shown schematically in FIG. 18. In the CMP process, the surface of the wafer on which the thin film is formed is made planarized through polishing. Next, the polishing agent adhered to the wafer is cleaned in the cleaning process. A resist is applied to the surface of the cleaned wafer and an exposure process is performed to expose the resist using a mask pattern. Next, an ashing process (not shown in the figure) is performed to develop the resist and form a resist pattern. In the etching process, a mask is used to perform etching on the thin film, which has been made planarized. This forms a thin-film pattern.

In the planarizing process described above, the wafer chuck 3 is used to support the wafer, in which an uneven thin film has been formed on a substrate by the deposition process. Polishing is performed while the polishing pad surface condition evaluating device 40 described above directly evaluates the surface condition of the polishing pad.

The following is a description of the specific embodiments of the present invention, with references to the drawings.

The examples below present surface condition evaluating methods and evaluating devices for CMP polishing pads used in semiconductor device production processes, as well as production methods and production devices for thin-film devices in which these are implemented.

<First Embodiment>

FIG. 18 is a schematic drawing centered on the CMP process in a semiconductor device production process. First, in a deposition process, a thin film needed to create the device is formed on a semiconductor wafer. If the deposition process is a production process for multi-layer wiring, conductor films formed from inter-layer insulative film and wiring film are layered.

When multiple thin films are formed in this deposition process, unevenness in the base film is planarized in the CMP process before subsequent layers of thin film are formed. This embodiment covers this CPM process. A wafer supported by the wafer chuck 3 is placed in contact with the polishing pad 1 mounted on the rotating polishing turntable. The polishing fluid (slurry) 5 is fed through the supply nozzle 5a to the pad 1 while CMP processing takes place.

As CMP processing is repeated on individual wafers, the pad 1 deteriorates so that, for example, a concentric wear 6 is formed. This worn section is corrected (dressed) with the conditioner 4. The polishing pad surface condition evaluation device 40 of the present invention is used to optimize the conditions used in this conditioning operation.

In the surface condition evaluation device 40 of the present invention, the pad 1 is illuminated with light from the light source 11. Optical information obtained from the illuminated region is detected using the detector 8. This detection signal is processed by the signal processor 9 to allow the surface condition of the pad 1 to be directly evaluated. The illumination is performed so that the light moves radially over the rotating pad 1, and the pad surface is scanned by the light beam. The detector 8 moves in tandem with the scanning of the light beam.

In the CMP processing operation, the output signal (pad surface condition evaluation information) processed by the signal processor 9 is sent as feedback to the conditioner 4 so that the conditioning conditions for the pad 1 are optimized.

Figure 3:
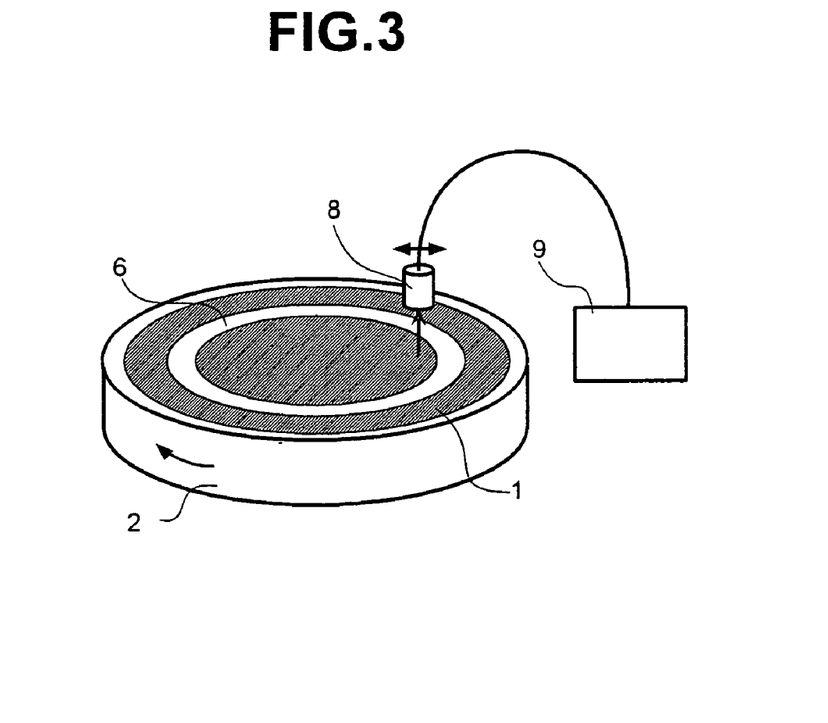
FIG. 3 is a schematic drawing showing a sample architecture of a polishing pad surface condition evaluation device according to the present invention.
Figure 4:
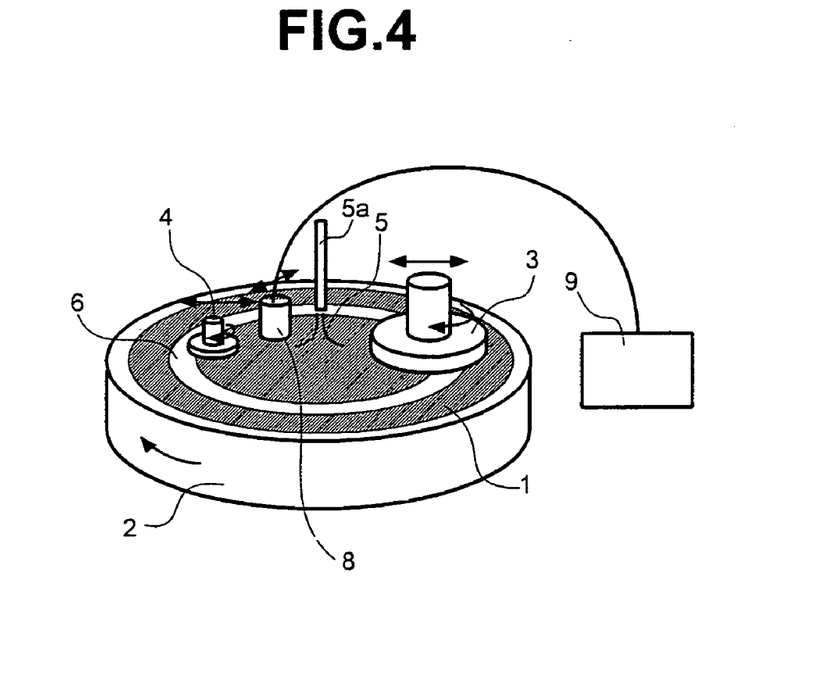
FIG. 4 is a schematic drawing showing another sample architecture of a polishing pad surface condition evaluation device according to the present invention.

FIG. 3 shows how the pad surface condition is evaluated while CMP processing is interrupted. FIG. 4 shows how the pad surface condition is evaluated during the processing. These figures show only the detector 8 and the signal processor 9 and omit illuminating means including the light source 11.

In the arrangements shown in FIG. 3 and FIG. 4, the relative positions of the detector 8 and the pad 1 are changed so that the distribution of pad surface conditions can be evaluated.

FIG. 3 and FIG. 4 show examples where relative positioning is changed through rotation of the pad 1 (rotation of the polishing turntable 2) and linear motion of the detector 8. However, other methods can be used as long as relative positioning can be changed.

In FIG. 4, surface conditions of the pad 1 can be evaluated in real time during CMP processing, and the conditioning conditions for the conditioner 4 can be controlled in real time.

Figure 5:
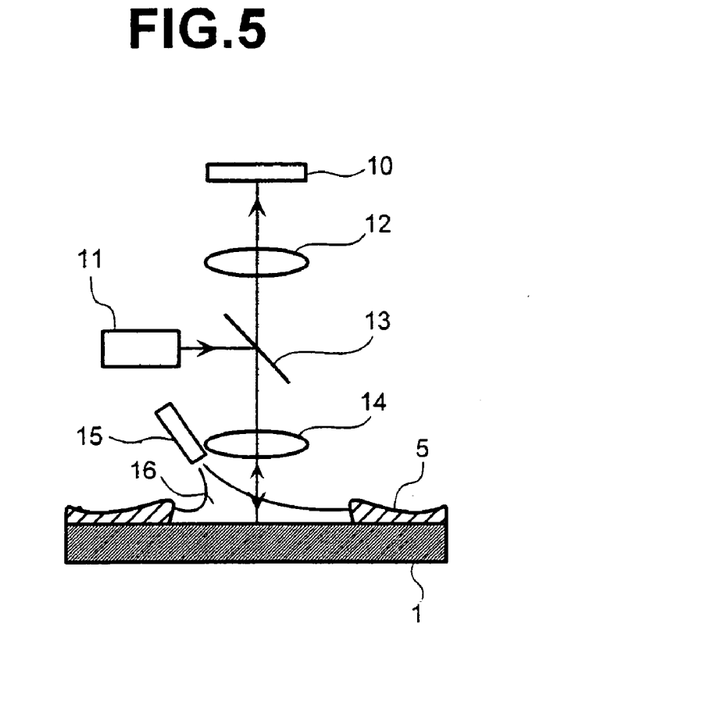
FIG. 5 is a schematic drawing of an optical system according to an embodiment of the present invention.
Figure 6:
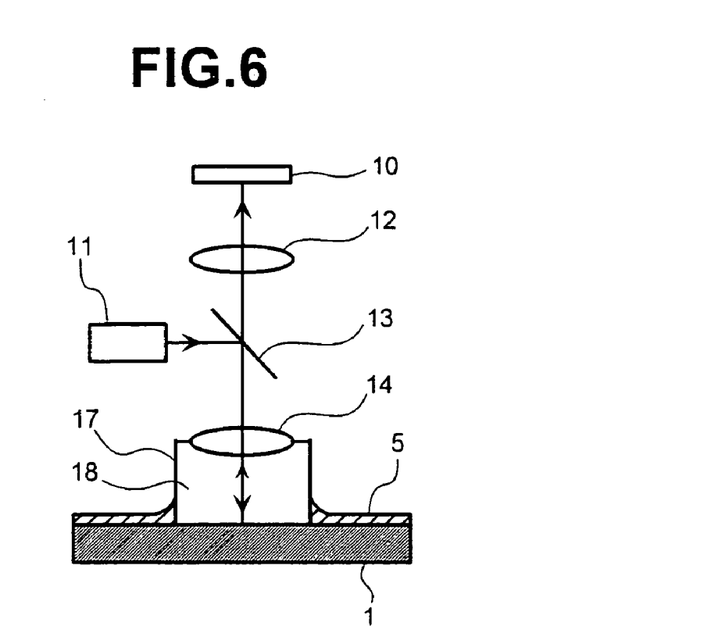
FIG. 6 is a schematic drawing of an optical system according to another embodiment of the present invention.

FIG. 5 and FIG. 6 show examples of detection optical systems for the present invention.

FIG. 5 shows a white light source (halogen lamp) or laser light source 11, a beam splitter 13, an objective lens 14, an focusing lens 12, a detector 10, and a gas blower nozzle 15. The figure also shows a slurry 5, which is a polishing fluid, and a compressed gas 16 blown out from the gas blower nozzle 15.

The light from the light source 11 passes through the beam splitter 13 and changes direction. It then passes through the objective lens 14 and illuminates the surface of the pad 1. The light reflected from the pad 1 passes through the objective lens 14 and is imaged in the detector 10.

This reflected light has different intensities and the like depending on the surface condition of the measured object. The intensity of the reflected light or image processing performed on the pad surface image are used to evaluate the pad surface condition. The presence of the slurry 5 on the pad surface will obstruct detection. To prevent this, the gas blower nozzle 15 is used to temporarily remove the slurry 5 from the illuminated region by blowing gas.

In addition to halogen lamps, the detection light source 11 can be a light source having a wide bandwidth such as xenon lamps. Also, laser lights having single or multiple wavelengths can be used.

In addition to a two-dimensional CCD sensor, the detector 10 can be a one-dimensional line sensor. Also, a non-CCD sensor can be used. The compressed gas 16 can be any gas such as nitrogen gas that does not affect processing of the product.

In FIG. 6, shows a method where, instead of blowing gas to temporarily remove the slurry 5, a tank 17 adequate for immersing the objective lens 14 and the pad surface is provided, and water or slurry is placed in the tank when detection of reflected light is performed.

Figure 11:
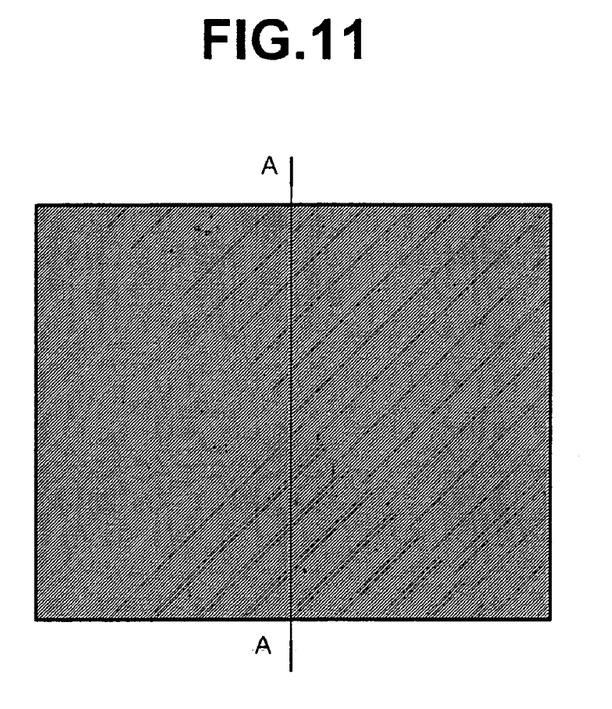
FIG. 11 is a drawing showing an example of an image of a good pad surface.
Figure 13:
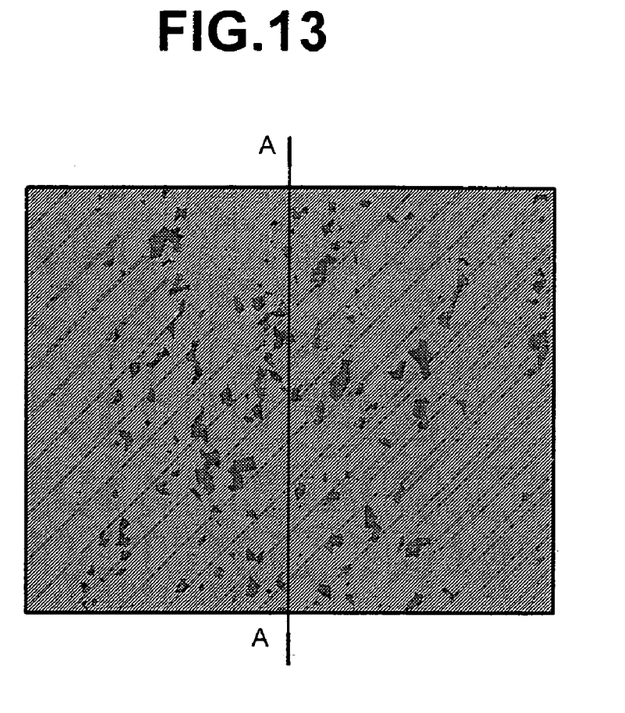
FIG. 13 is a drawing showing an example of an image of a deteriorated pad surface.

The relationship between the pad surface condition and the detection image will be described. FIG. 11 and FIG. 13 respectively show a detection image of good surface conditions with no noise and a detection image of bad conditions with a lot of noise.

Figure 12:
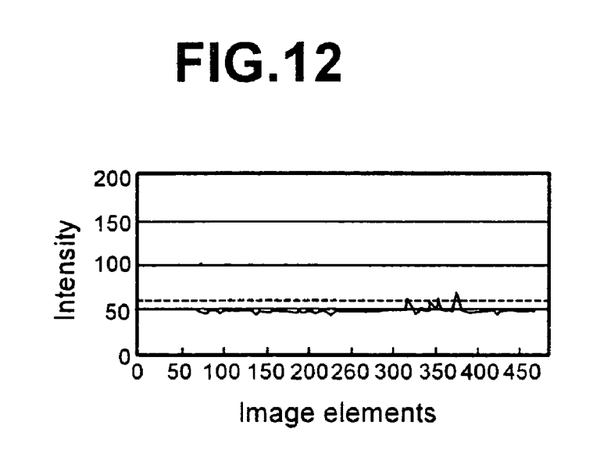
FIG. 12 is a drawing showing intensity distribution along the A—A line in the image from FIG. 11.
Figure 14:
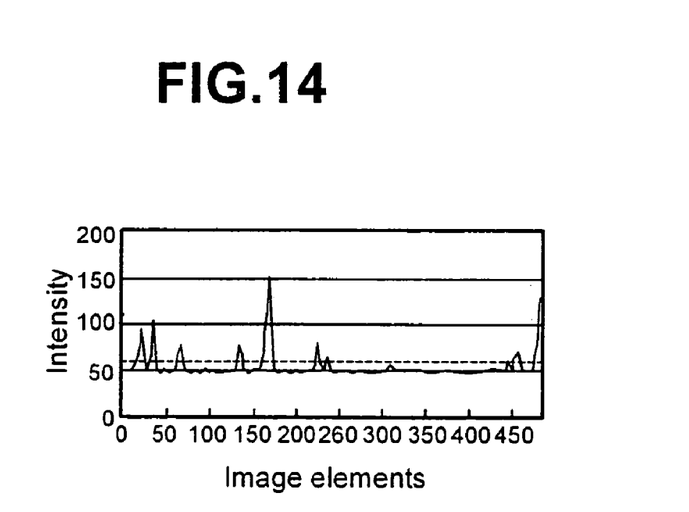
FIG. 14 is a drawing showing intensity distribution along the A—A line in the image from FIG. 13.

FIG. 12 and FIG. 14 show intensity profiles along the A—A cross-section from FIG. 11 and FIG. 13 respectively. The horizontal axis represents image element in the image and the vertical axis represents the signal intensity for the image element. These figures show that in both cases, there is an offset of about 50 and spiked peaks.

However, comparing these, it can be seen that the worn pad surface image (FIG. 14) has more spiked peaks with higher intensities compared with the good surface image (FIG. 12). The reasons for this difference will be described. When the pad surface is good, the surface is rough with few planarized areas. This causes light to be scattered, resulting in less reflected light. With a worn surface, the CMP process has made the pad surface planarized, so it is believed these areas reflect light and increase the number of peaks and their intensities in the detection image. Thus, pad surface conditions can be evaluated by detecting the number of peaks, the intensity of peaks, average intensity, and the like of the detection image.

Next, an example of a method for evaluating pad surface conditions using bi-level processing will be described.

Figure 15:
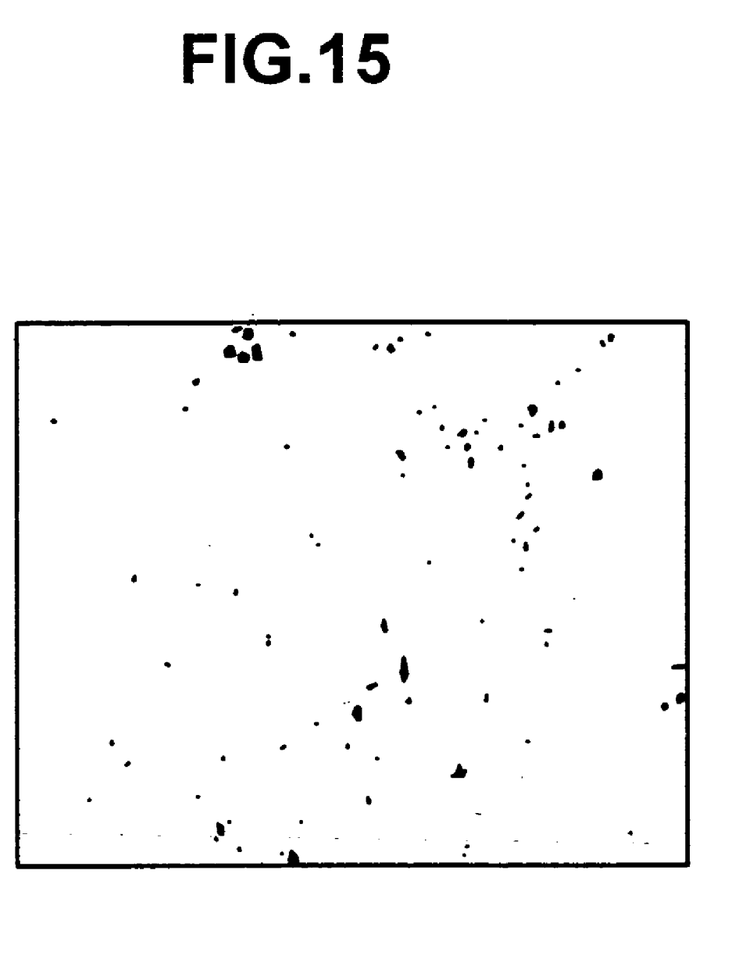
FIG. 15 is an image resulting from bi-level conversion of the image from FIG. 11.
Figure 16:
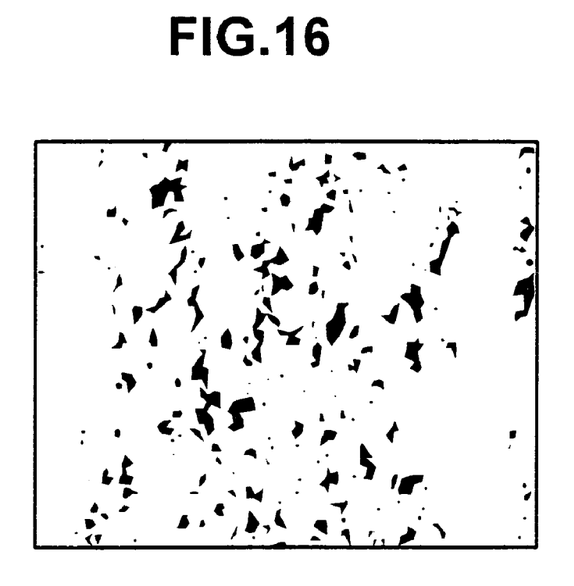
FIG. 16 is an image resulting from bi-level conversion of the image from FIG. 13.

First, a pad surface image (see FIG. 11 and FIG. 13) from the detector 10 is captured by a personal computer (PC). Bi-level conversion is performed on the captured image using a threshold value (the value indicated by the dotted lines in FIG. 12 and FIG. 14) set up beforehand or calculated from the detected image. The area ratio of the bi-level image (see FIG. 15 and FIG. 16) is calculated. FIG. 15 shows a bi-level image for a good pad surface based on FIG. 12. FIG. 16 shows a bi-level image for a worn pad surface based on FIG. 14. The calculated area ratio is correlated with the wear on the pad surface, and this correlation allows the surface condition of the pad to be evaluated. Performing bi-level conversion allows image characteristics to be made clear.

<Second Embodiment>

Figure 7:
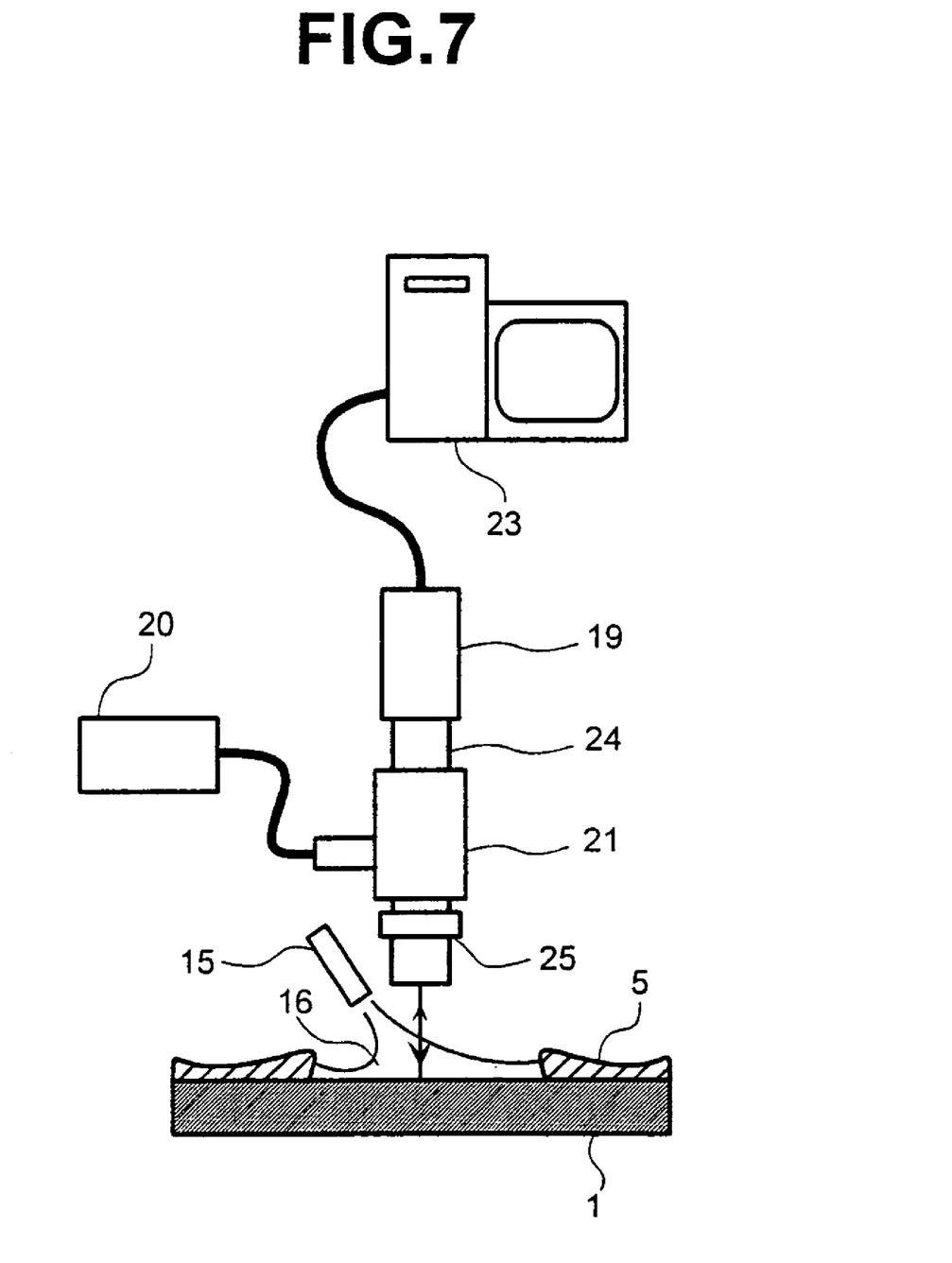
FIG. 7 is a schematic drawing of a detection device according to an embodiment of the present invention.

FIG. 7 shows an example of a specific device in which the pad evaluation method described above is implemented. The device includes a halogen light source or laser light source 20, an objective lens 25, a relay lens 24, a CCD camera 19, an AF (auto-focus) unit 21, a PC 23, and a gas blower nozzle 15. If the objective lens 25 has a large focal depth, the AF may not be needed. A non-CCD imaging element may also be used.

The CCD camera 19 is used to image the pad surface. This image is captured by the PC 23 and the image processing operation described above is performed to determine an area ratio.

<Third Embodiment>

Figure 8:
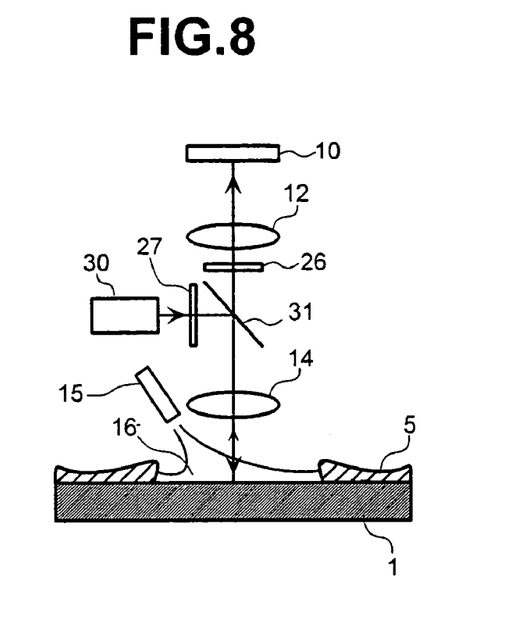
FIG. 8 is a schematic drawing of an optical system according to another embodiment of the present invention.

Next, an example in which a fluorescence observation system is used in the detection system will be described. FIG. 8 shows an example of the optical system. The optical system includes an excitation light source 30, a dichroic mirror 31, a filter 1 26, a filter 2 27, an objective lens 14, an focusing lens 12, a detector 10, and a gas blower nozzle 15.

The excitation light from the light source 30 is converted to a light with a desired wavelength range by the bandpass filter 2 27. The light then passes through the objective lens 14 by way of the dichroic mirror 31 and illuminates the surface of the pad 1. The excitation light causes light excitation from the pad 1, generating light with wavelengths different from that of the illumination. This light passes through the objective lens 14 and the bandpass filter 1 26, converting the light into a wavelength range different from that of the filter 2. This light is then imaged by the detector 10.

If contaminants, polishing particles, or the like is present on the pad surface, excitation light from the corresponding area will not be detected. Image processing on the intensity distribution image or intensities of excitation light can be used to evaluate the pad surface condition.

As in FIG. 5, the presence of slurry on the pad surface can obstruct detection. The gas blower nozzle 15 is used to temporarily remove the slurry 5 by blowing the compressed gas 16. It would also be possible to immerse the objective lens 14 as in FIG. 6.

The image processing can be performed using methods similar to those used in the detection systems shown in FIG. 5 and FIG. 6. With this fluorescence detection system, evaluation can be performed on contaminants, polishing particles, or the like, which cannot be detected with the detection systems shown in FIG. 5 and FIG. 6.

<Fourth Embodiment>

Figure 9:
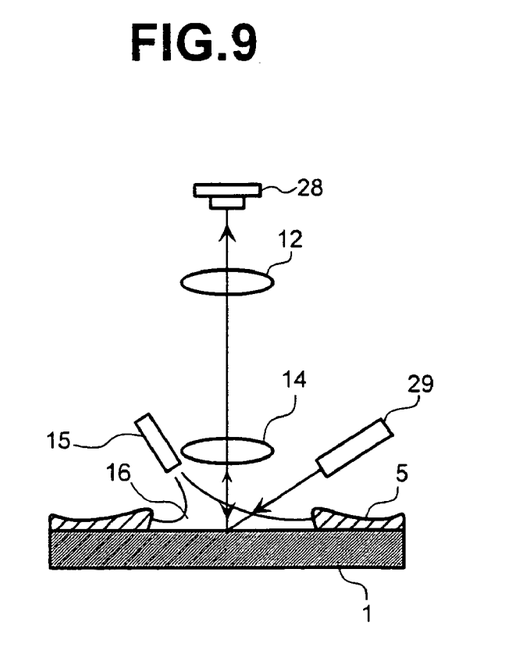
FIG. 9 is a schematic drawing of an optical system according to another embodiment of the present invention.

Next, an example in which a laser diffusion system is used in the optical system. FIG. 9 shows an example of the optical system. The optical system includes a laser light source 29, an objective lens 14, an focusing lens 12, a detector 28 (photomultiplier), and a gas blower nozzle 15.

The light from the light source 29 illuminates the surface of the pad 1 at an angle. The illumination is scattered on the surface of the pad 1. A portion of the scattered light passes through the objective lens 14 and is detected by the detector 10. The scattered light will having varying intensities and intensity distributions based on the surface condition of the object being inspected. Image processing is performed on the pad surface image or the diffused light intensities to evaluate the pad surface condition.

As in FIG. 5, the presence of the slurry 5 on the pad surface will obstruct detection. The gas blower nozzle 15 temporarily removes the slurry 5 by blowing the compressed gas 16. It would also be possible to perform detection by immersing the objective lens 14 as in FIG. 6.

With the diffusion system, the shape (planarity) of the pad surface can be evaluated, as in the detection systems in FIG. 5 and FIG. 6. The image processing can be performed in the same manner as in the optical systems shown in FIG. 5 and FIG. 6.

In the fluorescence detection system and the laser diffusion system described above, the methods for detecting pad surface condition distribution, evaluation of detection results, and accompanying operations are performed in the same manner as in the optical systems shown in FIG. 5 and FIG. 6.

<Fifth Embodiment>

Figure 10:
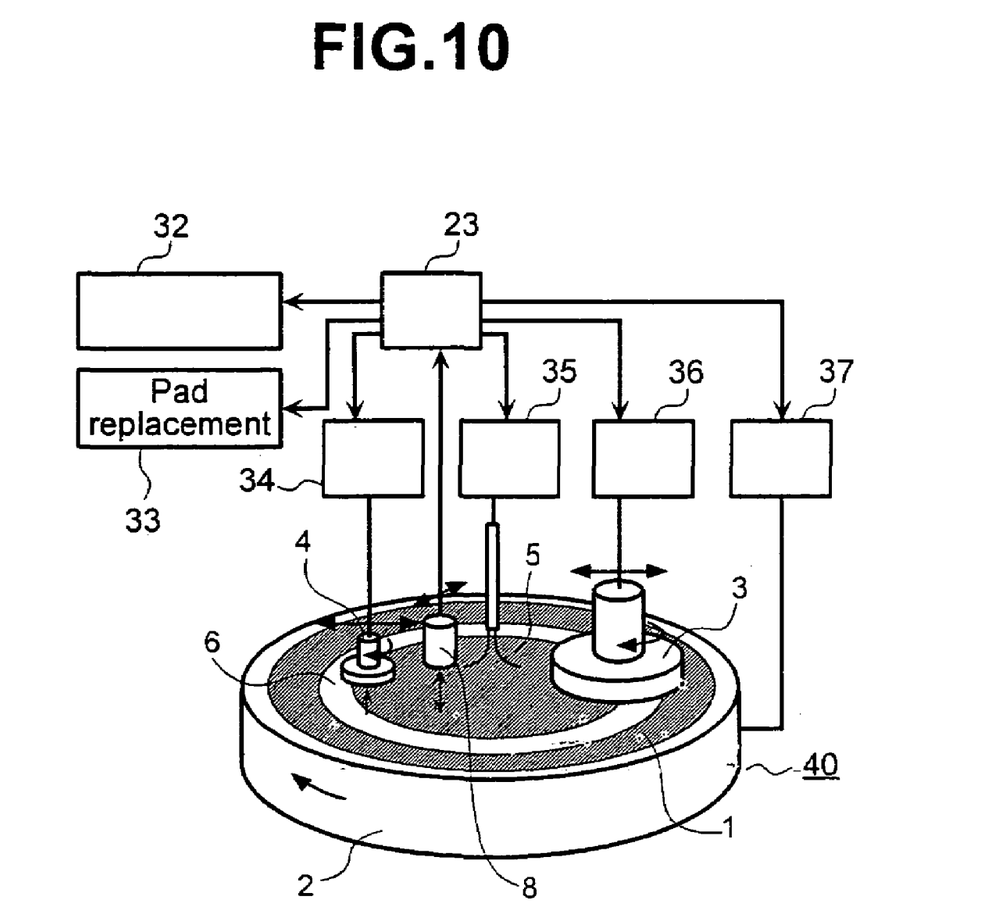
FIG. 10 is a schematic drawing of a sample feedback destination for results from pad surface condition evaluation according to an embodiment of the present invention.

FIG. 10 shows an example of an output destination for processing results from a CMP device widely known in the art that includes the polishing surface condition evaluation device 40 equipped with an optical system described above. The figure shows a PC 23 for image detection and image processing, a display 32, a pad replacement unit 33, a conditioning control unit 34, a slurry supply control unit 35, a wafer chuck control unit 36, and a polishing turntable control unit 37.

An example of how the polishing pad surface condition evaluation device 40 according to the present invention can be used in a CMP process was described in summary earlier, with reference to FIG. 18.

Figure 19:
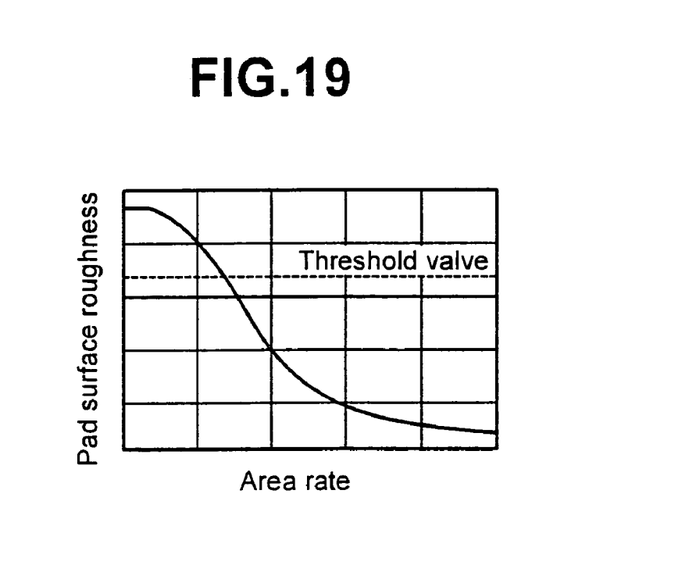
FIG. 19 is a schematic drawing showing an example of correlation between area ratios resulting from image processing and pad surface roughness.

If the output from the processing results from the image detection and signal processing PC 23 is sent to the display 32, the evaluation of the calculation results can be performed, for example, by comparing the area ratio with a threshold value set up beforehand. For example, as shown in FIG. 19, the correlation between area ratio and pad surface roughness, used as a parameter indicating pad wear, can be determined beforehand. When the area ratio exceeds a threshold value set up beforehand, a warning can be displayed on the display.

If the detection output from the detector 8 of the polishing pad surface condition evaluation device 40 is processed by the image detection and signal processing PC 23, and the results are sent to the conditioning control unit 34 as feedback for conditioning conditions such as contact pressure of the conditioner 4 to the pad, rotation speed, reciprocating motion, and the like, the correlation with the recovery from wear provided by conditioning is determined beforehand, and this correlation is used to optimize conditioning conditions.

Figure 20:
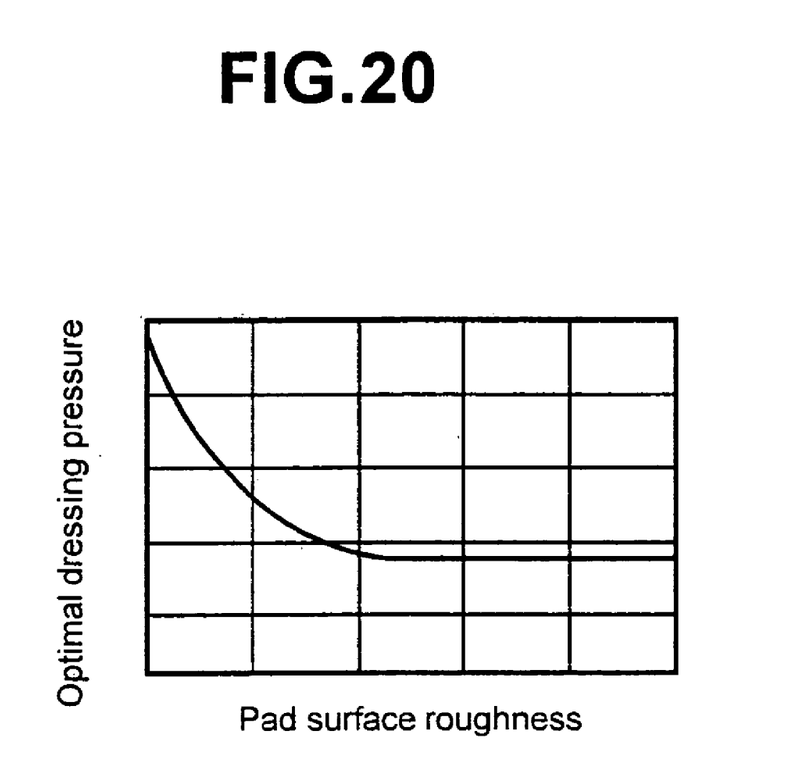
FIG. 20 is a schematic drawing showing an example of correlation between pad surface roughness and optimal conditioning conditions.

For example, in addition to the correlation shown in FIG. 19, the pad wear shown in FIG. 20 can be used as a parameter to determine the correlation between the pad surface roughness and the optimal conditioning pressure for pad surface condition recovery. Then, the conditioning pressure can be optimized based on the area ratio. Of course, it would also be possible to determine the correlation between the area ratio and the optimal conditioning pressure directly.

In addition to conditioning pressure, other conditioning conditions such as conditioning rotation speed, reciprocating motion, and the like can be optimized by detecting the distribution of wear on the pad surface, i.e., the distribution of the area ratio described above over the pad surface.

Methods similar to those involved in conditioning described above can be used if the detection output from the detector 8 is processed by the image detection and signal processing PC 23 and the results are output to the wafer chuck control unit 36 as feedback for polishing conditions such as the contact pressure on the pad, rotation speed, and reciprocating motion of the wafer chuck 3, and the rotation speed of the polishing turntable 2.

Pad replacement timing is determined by determining when pad surface conditions cannot be restored even if conditioning conditions are optimized. The evaluation methods for the feedback destinations described above are examples, and the evaluation methods are not restricted to those presented above. Also, the evaluations and the operations accompanying the evaluation results described above can be performed manually by the operator of the device or can be performed automatically.

It would also be possible for the results from the image detection and signal processing PC 23 processing the detection output from the detector 8 to be output to the slurry supply control unit 35 so that the slurry supply can be controlled. Furthermore, the processing results can be output to the polishing turntable control unit 37 so that the rotation of the polishing turntable is controlled.

Pad evaluation devices equipped with the detection systems described in the examples above can be built into devices or can be installed within devices as necessary.

With the embodiments of the present invention described above, high-precision evaluation of polishing pad surface conditions can be performed directly and the evaluation data can be used to provide high-precision polishing process management. Also, by having this method for evaluating polishing pad surface conditions built into a CMP processing device, the process throughput can be improved. For example, in methods for producing semiconductor devices on a silicon wafer and in CMP processes on production lines, high-precision evaluation of polishing pad surfaces can be directly performed, thus improving process throughput.

The invention may be embodied in other specific forms without departing from the spirit or essential characteristics thereof. The present embodiment is therefor to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for evaluating polishing pad surface conditions comprising the following steps:
   removing polishing fluid adhered to a polishing pad surface for at least an area of said polishing pad surface;
   illuminating with light said area of said polishing surface from which said polishing fluid was removed;
   imaging said illuminated area by an optical imaging unit and obtaining an image of said polishing pad surface;
   evaluating deterioration of said polishing pad surface by processing said surface image to convert said surface image into a bi-level image, and by then using an area ratio of said bi-level image to evaluate the deterioration of said polishing pad surface; and
   displaying results from said evaluation on a monitor.

2. A method for evaluating polishing pad surface conditions as described in claim 1,
   wherein removal of polishing fluid adhered to said polishing pad surface is performed by flowing gas onto said polishing pad surface.

3. A method for evaluating polishing pad surface conditions as described in claim 1,
   further comprising a step for outputting information of said evaluation results to conditioning means for said polishing pad.

4. A method for evaluating polishing pad surface conditions, comprising the following steps:
   removing polishing fluid adhered to a polishing pad surface for at least an area of said polishing pad surface;
   illuminating with light said area of said polishing surface from which said polishing fluid was removed;
   imaging said illuminated area by an optical imaging unit and obtaining an image of said polishing pad surface;
   evaluating deterioration of said polishing pad surface by processing said surface image;
   displaying result from said evaluation on a monitor;
   detecting fluorescence generated by said polishing pad due to said illumination;
   further evaluating deterioration of said polishing pad surface based on an intensity signal of said detected fluorescence; and
   outputting results from said evaluation based on the intensity signal.

5. A method for evaluating polishing pad surface conditions as described in claim 4, wherein a fluorescence image is obtained from the fluorescence generated by said polishing pad; and deterioration due to contaminants on said polishing pad surface is evaluated based on said fluorescence image.

6. A device for evaluating polishing pad surface conditions, comprising:
   means for removing polishing fluid adhered to at least an area of a polishing pad surface;
   means for illuminating said area on said polishing pad surface from which said polishing fluid was removed by said polishing fluid removing means;
   means for capturing images of said area illuminated by said illuminating means and obtaining an image of said polishing pad surface;
   first evaluating means for evaluating deterioration of said polishing pad surface by processing said image of said polishing pad surface obtained through said image capturing means; and
   first outputting means for outputting information of results from said evaluating means;
   wherein said first evaluating means performs bi-level conversion on said image obtained through said image capturing means to provide a bi-level image; and
   deterioration of said polishing pad surface is evaluated based on an area ratio of said bi-level image.

7. A device for evaluating polishing pad surface conditions as described in claim 6, wherein
   said polishing fluid removing means removes polishing fluid adhered to said polishing pad surface by blowing a gas onto said polishing pad surface.

8. A device for evaluating polishing pad surface conditions as described in claim 6, further comprising:
   means for outputting information of results from said evaluation to conditioning means for said polishing pad.

9. A device for evaluating polishing pad surface conditions, comprising:
   means for removing polishing fluid adhered to at least an area of a polishing pad surface;
   means for illuminating said area on said polishing pad surface from which said polishing fluid was removed by said polishing fluid removing means;
   means for capturing images of said area illuminated by said illuminating means and obtaining an image of said polishing pad surface;
   first evaluating means for evaluating deterioration of said polishing pad surface by processing said image of said polishing pad surface obtained through said image capturing means;
   first outputting means for outputting information of results from said evaluating means;
   means for detecting fluorescence generated by said polishing pad due to illumination from said illuminating means;
   second evaluating means for evaluating deterioration of said polishing pad surface based on an intensity signal of fluorescence detected by said fluorescence detecting means; and
   second outputting means for outputting information of results from said evaluation.

10. A device for evaluating polishing pad surface conditions as described in claim 9, wherein said fluorescence detecting means obtains a fluorescence image; and said second evaluating means evaluates deterioration of said polishing pad surface due to contaminants based on the fluorescence image obtained by said fluorescence detecting means.

11. A device for evaluating polishing pad surface conditions as described in claim 9, wherein said second outputting means displays information of results evaluated by said second evaluating means to a display.

* * * * *